(12) United States Patent
Jung et al.

(10) Patent No.: US 11,039,945 B2
(45) Date of Patent: Jun. 22, 2021

(54) STENT PROSTHESIS

(71) Applicant: MEDICUT STENT TECHNOLOGY GMBH, Pforzheim (DE)

(72) Inventors: Johannes Jung, Pforzheim (DE); Aryan Fallahi, Pforzheim (DE)

(73) Assignee: MEDICUT STENT TECHNOLOGY GMBH, Pforzheim (DE)

( * ) Notice: Subject to any disclaimer, the term of this patent is extended or adjusted under 35 U.S.C. 154(b) by 112 days.

(21) Appl. No.: 15/525,337

(22) PCT Filed: Nov. 10, 2015

(86) PCT No.: PCT/EP2015/025081
§ 371 (c)(1),
(2) Date: May 9, 2017

(87) PCT Pub. No.: WO2016/074799
PCT Pub. Date: May 19, 2016

(65) Prior Publication Data
US 2017/0319364 A1    Nov. 9, 2017

(30) Foreign Application Priority Data
Nov. 11, 2014   (DE) ..................... 10 2014 016 588.4

(51) Int. Cl.
*A61F 2/915* (2013.01)

(52) U.S. Cl.
CPC .... *A61F 2/915* (2013.01); *A61F 2002/91525* (2013.01); *A61F 2002/91558* (2013.01);
(Continued)

(58) Field of Classification Search
None
See application file for complete search history.

(56) References Cited

U.S. PATENT DOCUMENTS

| 5,843,175 A | 12/1998 | Frantzen |
| 5,938,697 A | 8/1999 | Killion et al. |

(Continued)

FOREIGN PATENT DOCUMENTS

| CN | 102497838 A | 6/2012 |
| DE | 1974688 U | 12/1967 |

(Continued)

OTHER PUBLICATIONS

First Office Action received from Chinese Patent Office dated Aug. 28, 2018.

(Continued)

*Primary Examiner* — Leslie Lopez
(74) *Attorney, Agent, or Firm* — Hudak, Shunk & Farine Co. LPA

(57) ABSTRACT

A stent for use in hollow tubular organs, comprising a continuous tubular or cylindrical inner cavity which is delimited by a wall. The wall is formed in a tubular or cylindrical manner about an axis which runs in a longitudinal direction and has a structure which surrounds the wall. The structure is made of elements, and the elements are made of loops which are arranged about the longitudinal axis in the radial direction. The elements are rigidly connected via connection points such that a tubular or cylindrical single-piece wall structure is produced, and the stent has acute angles in the region of the connection points.

18 Claims, 7 Drawing Sheets

(52) U.S. Cl.
CPC ............... *A61F 2220/0025* (2013.01); *A61F 2230/0045* (2013.01); *A61F 2250/0098* (2013.01)

(56) References Cited

U.S. PATENT DOCUMENTS

| | | | |
|---|---|---|---|
| 8,647,378 B2 | 2/2014 | Mews et al. | |
| 2004/0044400 A1* | 3/2004 | Cheng | A61F 2/91 623/1.16 |
| 2005/0187610 A1 | 8/2005 | White et al. | |
| 2005/0273157 A1* | 12/2005 | Pinchasik | A61F 2/915 623/1.15 |
| 2006/0004437 A1* | 1/2006 | Jayaraman | A61F 2/91 623/1.16 |
| 2006/0173529 A1 | 8/2006 | Blank | |
| 2008/0249599 A1 | 10/2008 | Allen et al. | |
| 2008/0281397 A1 | 11/2008 | Killion et al. | |
| 2009/0036977 A1 | 2/2009 | Rassat et al. | |
| 2009/0248132 A1 | 10/2009 | Bloom et al. | |
| 2009/0248133 A1* | 10/2009 | Bloom | A61F 2/2418 623/1.15 |
| 2012/0330000 A1 | 12/2012 | Hyodoh et al. | |

FOREIGN PATENT DOCUMENTS

| | | |
|---|---|---|
| DE | 196 53 708 A1 | 4/1998 |
| EP | 0 903 123 A1 | 3/1999 |
| EP | 2 438 872 A1 | 4/2012 |
| FR | 2768919 A1 | 4/1999 |
| JP | 2002505149 A | 2/2002 |
| JP | 2003523792 A | 8/2003 |
| JP | 2005519672 A | 7/2005 |
| WO | 9725000 A1 | 7/1997 |
| WO | 0126583 A1 | 4/2001 |

OTHER PUBLICATIONS

European Communication, with translation, dated Oct. 25, 2019.
Office Action from Japanese Patent Office dated Sep. 20, 2019.
Second Office Action received from Chinese Patent Office dated May 13, 2019.

* cited by examiner

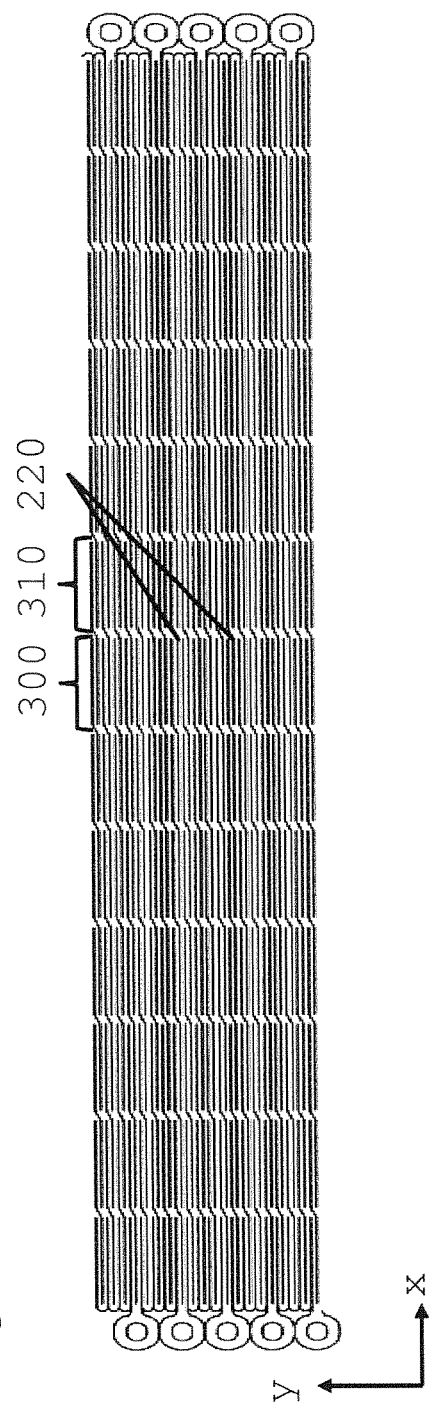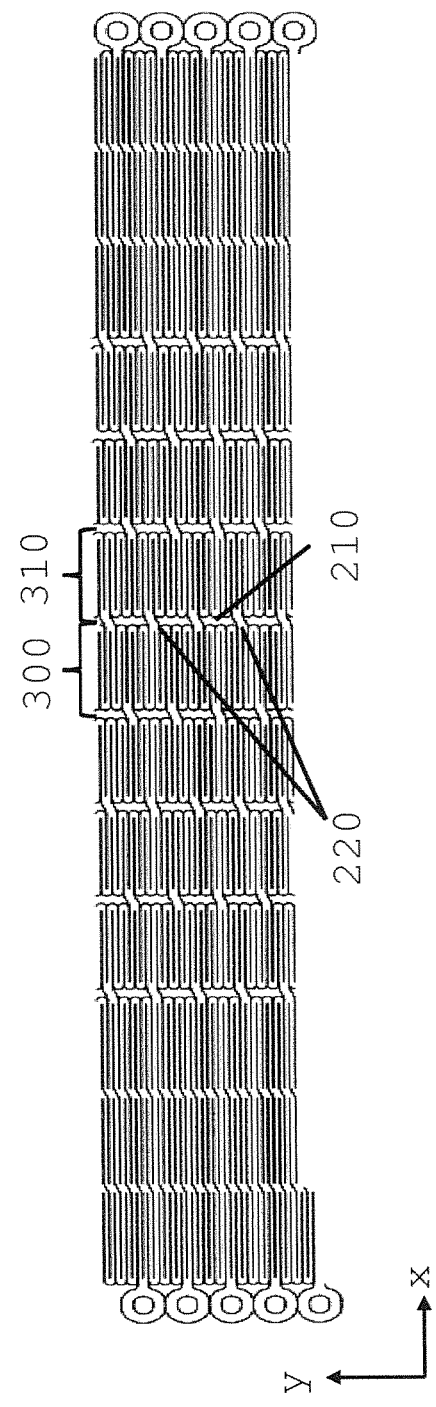

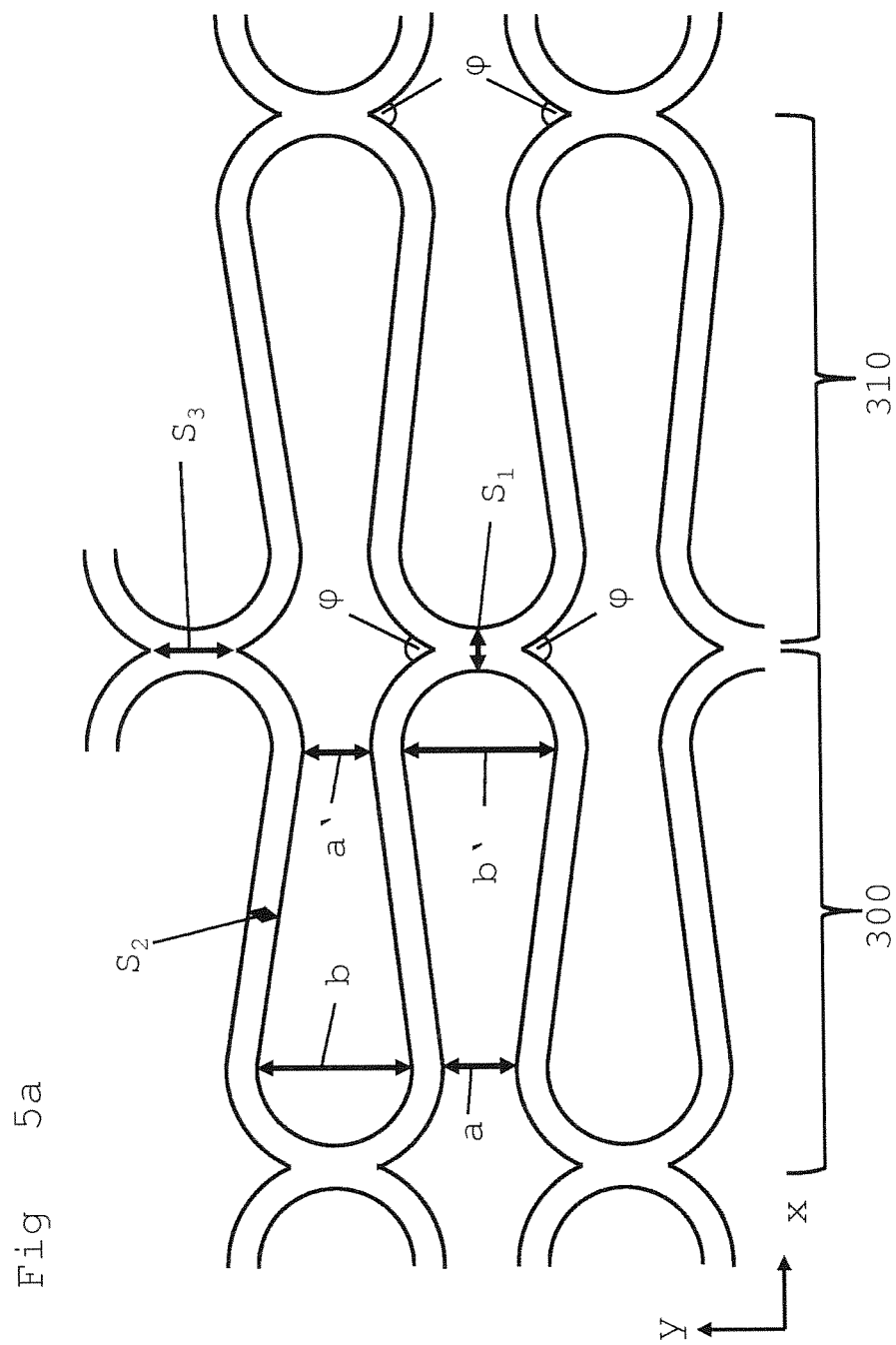

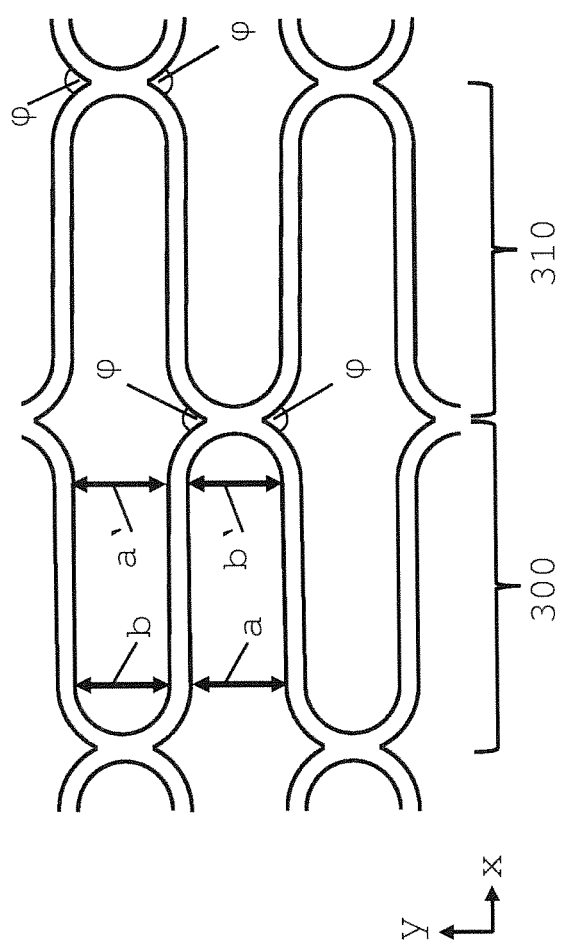
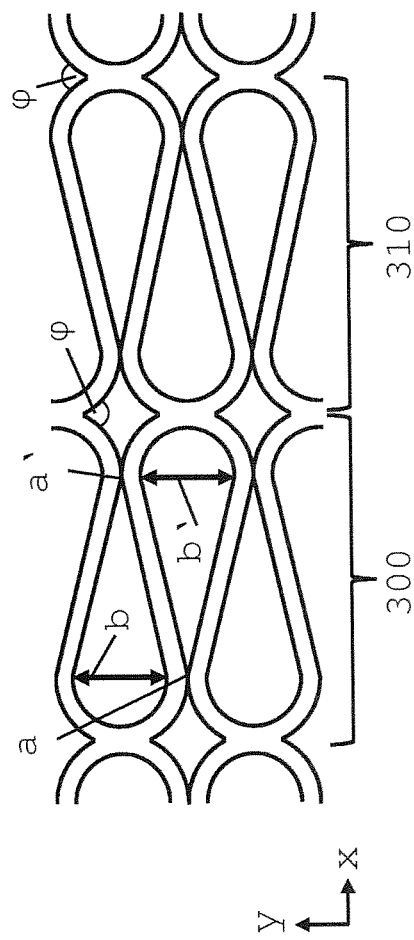
Fig 5b
Fig 5c

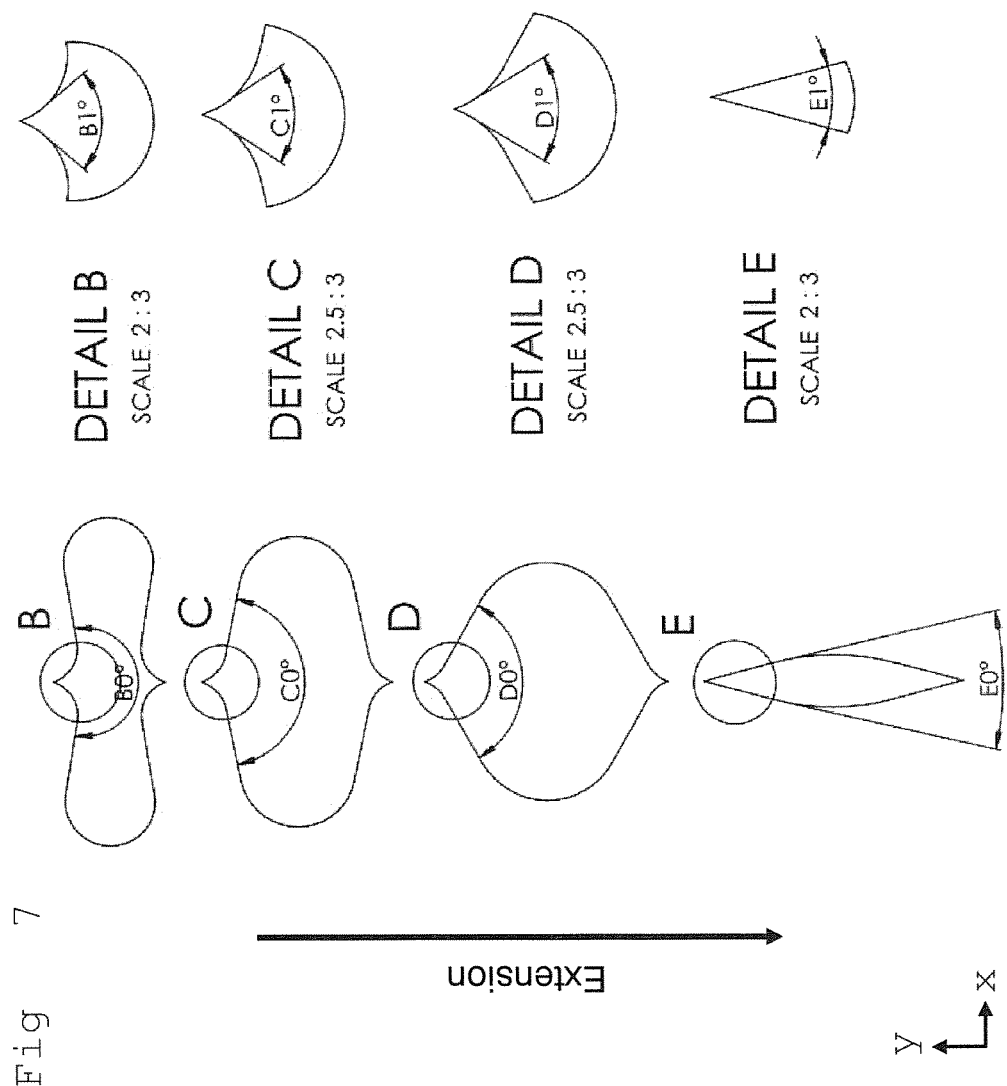

STENT PROSTHESIS

FIELD OF THE INVENTION

The invention concerns a stent for use in tubular hollow organs with a continuous, interior, tubular or cylindrical cavity bounded by a wall, wherein the wall is configured to be tubular or cylindrical and extending about an axis running in the longitudinal direction and comprises a structure running about the wall. The structure is formed from elements and the elements are firmly joined by connection points to produce a single-piece tubular or cylindrical wall structure.

BACKGROUND OF THE INVENTION

Stents are used among other things as prostheses for widening, holding open, and stabilizing in tubular hollow organs such as blood vessels. Generally such stents comprise lattices or spiral-shaped structures made of material webs. Usually areas free of material are formed between the material webs, making it possible for tissue to grow in at the implant site. Such stents are described for example in the document DE A 197 46 88.

Usually such prostheses are used among other things for treatment of stenoses, where the prostheses are employed to widen and hold open the wall of a vessel, such as an artery, so that an adequate flow is assured through the vessel. The prostheses generally have very slight wall thicknesses, although a certain radial rigidity must be present so that the shape of the prosthesis is maintained in the desired form after implantation in a vessel. Besides a radial rigidity, the prosthesis should furthermore have an adequate bending strength, making it possible for the prosthesis to sufficiently adapt to the partly curved shape and the movements of the section of vessel in which the prosthesis is implanted.

With prostheses of the prior art the problem occurs that a prosthesis implanted in bendable vessel regions, such as the region of the joints, is subjected to substantial compressive, tensile, and rotary movements. In addition, frictional forces also act on the intima of the blood vessels in the region of the joints. The mentioned compressive, tensile, and rotary movements weaken the material webs of the prosthesis, so that this may result in breakage and individual detachments of fragments of the prosthesis. This may lead to injuries to the vessel wall, restenosis, e.g., by formation of scar tissue on the vessel wall, or even the formation of an aneurysm. Sometimes embolisms may also be triggered in this way.

Usually the prosthesis is introduced in a compressed state during its implantation in the vessel and it then expands at the treatment site, which is generally done with the aid of a balloon catheter. A balloon catheter is also usually employed for the positioning of the prosthesis in the vessel. However, it is also possible to use a self-expanding prosthesis, which is introduced into the vessel in a compressed state by means of a catheter and then released at the desired site of the vessel, which is accomplished during a simultaneous expansion of the prosthesis.

Two fundamental stent techniques or structures are known from the prior art, namely, the so-called Open Cell Design, as represented in FIG. 1, showing the prior art, and the Closed Cell Design, as represented in FIG. 2, showing the prior art. The so-called Open Cell Design is a flexible design, while the Closed Cell Design is a relative rigid design of the stent.

Generally the structure of these stents is substantially lattice-like, and this lattice may have the most diverse of configurations. For example, the structure of the rigid design is domino-shaped or rhomboidal, the corner points of one rhomboid being joined to those of other rhomboids. The drawback to this rigid structure is that it buckles under bending, so that the liquid flow (e.g., the flow of blood) has a tendency to swirl in flowing past the kink point, forming a turbulent flow in the kink region instead of the desired laminar flow. This turbulent flow usually leads to unwanted deposits, sometimes a clumping together of erythrocytes, with possible consequences of a neointima hyperplasia and arteriosclerosis, or even symptomatic restenosis. A further drawback of this design is that, upon expanding of the stent in the radial direction, the so-called connectors at the rhomboid (domino) corner points may be torn loose. However, one benefit of this rigid design is that a stent, if placed wrongly or inaccurately inside a vessel, can be again pulled into the catheter or the chamber of a catheter. This is not possible with the so-called flexible or Open Cell Design, because the stent will break if drawn back into the catheter or the chamber. This also has to do in particular with the fact that, in the flexible design, interconnected stent elements are held together by means of so-called connectors, but the stent elements are always linked together in a chain by at least one nonconnected point. However, the benefit of the flexible design is that a kinking of the overall stent is for the most part prevented at bending sites. The radial strength of the flexible stent design, i.e., the strength resisting the radially inwardly directed force of the vessel, is also less than that of the rigid stent design.

Other stents are known from the prior art, which are formed from interwoven wires. The benefit of these stents is that they are flexible, i.e., do not kink at bending sites and thus have a high radial strength. Such stents are described for example in the document US 2012/0330398 A1. The drawback to such stents, however, is that the interwoven wire has crossing points, which might injure the inner walls of the vessels. Since these crossing points are not smooth, slight nonlaminar turbulence may occur in this way, which may lead to unwanted deposits, e.g., due to the aggregation of erythrocytes, from which restenosis may develop.

Furthermore, a stent is described in DE 196 53 708 A1 having a tubular/cylindrical basic shape with numerous breakthroughs, which are surrounded by expandable structure elements having the shape of flattened rings. These expandable elements are formed by narrow weblike encircling regions with rectangular cross section and are distinguished in that they enclose a recess in ring-like manner. The weblike regions surrounding an expandable element are formed by multiple S-shaped curves. Each time they enclose a recess such that opposite weblike regions neighboring each other in the tangential direction of the same or a neighboring recess are arranged in mirror symmetry. Between the recesses arranged on the envelope surface of the stent and neighboring each other in the axial (longitudinal) and tangential (transverse) direction there are provided connection regions/connectors which mechanically couple together the respective expandable regions. These connection regions/connectors have a cross-like conformation, while the individual arms of the cross have the shape of arc segments.

A similar structure is also described in EP 0 903 123 A1. This discloses a stent which comprises a plurality of longitudinally situated bands along one longitudinal axis, wherein each band has the shape of a continuous wave running along a segment line parallel to the longitudinal axis. A plurality of connection elements/connectors holds the bands together in a tubular structure. One such longitudinal band of the stent is connected to a neighboring band at a plurality of periodically occurring sites.

FR 2 768 919 A1 describes a stent with a one-piece tubular structure. Certain lines encircle the stent and these lines are held together each time by means of connectors, so-called "tronçons intermédiaires" [intermediate pieces] or "barrettes de liaison" [connection bars], thus forming the one-piece structure of the stent (see FIG. 7 and FIG. 8 of D1).

WO 01/26583 A1 describes a stent which is composed of a plurality of cells, which in turn run radially about the stent. The cells here are formed from a plurality of braces, which are joined together. In FIG. 13 of D2 there is also a connector present here in the region 54i, which joins the individual cells together.

U.S. Pat. No. 5,843,175 A1 describes a stent with a cylindrical configuration of braces which can be installed in arteries during operations. Individual braces are held together here by means of connectors ("links" in English, reference 180).

U.S. Pat. No. 5,938,697 A1 describes a conical tubular stent for use in vessels such as arteries. The stent according to this document always consists of open regions which are held together by means of connectors, as well as closed regions.

In EP 2 438 872 A1 a stent is disclosed with a basic body of at least two webs and at least two deflection sites opposite each other in the axial direction, at which an adjusting means can be placed in order to widen the basic body in the circumferential direction.

On account of the structural conformation of the aforementioned stents in the region of the connectors, which comprise arc segments in part, a ripping of the structure may occur upon stretching or expansion in this region. Moreover, kinks can also occur upon bending of the stent in the region of the connectors on account of the length of these connectors, which may damage the vessel walls, or this can lead to nonlaminar turbulence, as already described above.

One problem which the invention proposes to solve is to overcome the drawbacks of the prior art, in particular, the stent according to the invention should not form kinks upon bending. Furthermore, the stent should be able to be pulled back into the chamber of a catheter without breaking, and possess smooth top/inner surfaces. Moreover, an increasing of the radially outwardly directed forces of the stent should be achieved.

SUMMARY OF THE INVENTION

The problem is solved by a stent with a continuous, interior, tubular or cylindrical cavity bounded by a wall, wherein the wall is configured to be tubular or cylindrical and extending about an axis running in the longitudinal direction (x) and comprises a structure running about the wall, wherein the structure is formed from elements and the elements are formed from loops, which are arranged substantially in the radial direction (y) about the longitudinal axis, and they have loop peaks and loop valleys arranged in alternating manner and running substantially parallel to the longitudinal direction (x), so that an element is firmly connected to the preceding or following element by connection points in the region of the loop valleys of the elements and the loop peaks of the following elements and in the region of the loop peaks of the elements and the loop valleys of the preceding elements in order to produce a one-piece tubular or cylindrical wall structure, characterized in that the loop peaks and the opposite loop valleys in the longitudinal direction stand in direct contact or overlap each other and each time at the connection points a web $S_1$ running substantially parallel to the longitudinal direction (x) and a web $S_3$ running substantially parallel to the radial direction (y) is formed, having a web $S_2$ in the region of the loop line between the loop peaks and the loop valleys and acute angles ($\varphi$) are present in the region of the connection points between loop valleys and loop peaks. The dependent claims indicate advantageous modifications and preferred embodiments.

According to the invention, a stent is provided with a continuous, interior, substantially tubular or cylindrical cavity bounded by a wall, wherein the wall is configured to be substantially tubular or cylindrical and extending about an axis running in the longitudinal direction. The wall comprises an encircling structure, and the structure is formed from elements. According to the invention, the elements of the stent are formed from loops, which are arranged substantially in the radial direction about the longitudinal axis, and they have loop peaks and loop valleys arranged in alternating manner and running substantially parallel to the longitudinal direction, so that the element is firmly connected to the preceding or following element by connection points or contact points in the region of the loop valleys of the element and the loop peaks of the following elements and in the region of the loop peaks of the element and the loop valleys of the preceding element in order to produce a one-piece tubular or cylindrical wall structure. Moreover, the stent according to the invention has acute angles $\varphi$ in the region of the connection points or contact points between loop valleys and loop peaks. This angle $\varphi$ is formed from the loop curves meeting at the connection points, namely, the tangents of the curves. Typically, these angles are less than 45°, 40°, 35°, 30°, especially less than 20°, while less than 15° or 10° is especially preferred, as regards the expanded stent.

By loops is meant here substantially open loops, such as are used in cordage, where this loop is known as a bay. The elements can constitute a plurality of members lying against each other, neighboring and firmly joined to each other, these members being arranged as rings or substantially radially about the longitudinal axis of the stent. However, the element can also be formed as a helix, a coil, a spiral, a screw, or a segment of the aforementioned structures. One turn or one revolution about the radial axis can constitute an element. A turn denotes here a (circular) pass of a helix, coil, spiral or screw. However, the structure can also be formed as a double helix. In this case, each helix constitutes one element.

In the sense of the invention, we are assuming a stent in the non-expanded condition. However, this does not rule out the stent according to the invention from having the following or above mentioned qualities also in an expanded or partly expanded condition. However, the stent according to the invention which should be suitable for use in hollow tubular organs has a corresponding shape so that it can be introduced into the corresponding hollow organ. Whether the stent of the invention is then expanded further, or can be so expanded, serves merely for the stability of the hollow organ, or serves to hold open the hollow organ, will depend on the goal to be accomplished with the treatment or therapy.

Surprisingly, it has been found that because of the structure of the stent according to the invention, it does not kink at bending points or when bending.

It is likewise possible according to the invention to pull the stent according to the invention back into the catheter or the chamber of the catheter when it has been placed wrongly or inaccurately in the vessel by means of a catheter or the like. In this way, the implantation of the stent according to the invention is easier and less prone to error.

The stent according to the invention is advantageously made from a single piece of tubular material, advantageously by cutting with a laser technique. This produces totally smooth, radially outwardly directed (mural) surfaces or inner (luminal) surfaces directed toward the inside of the stent. Thanks to the totally smooth inner surface, practically no turbulent flow occurs as is caused by deposits at uneven sites, so that instead a desired laminar flow within the stent is established. Trauma to the vessel wall is also practically avoided thanks to the totally smooth surface.

The stent according to the invention comprises each time at the connection points a web $S_1$ running substantially parallel to the longitudinal direction and a web $S_3$ running substantially parallel to the radial direction. Moreover, the stent according to the invention comprises a web $S_2$ in the region of the loop lines between the loop peaks and the loop valleys.

The connection points or contact points according to the invention should not be confused with connectors as are known from the prior art. The connectors of the prior art always have a certain length in the longitudinal direction of the stent, so that for example a spacing is always present for example between loop peaks and opposite loop valleys in the longitudinal direction. In contrast with this, the connection points according to the invention preferably have no such spacing, so that the loop peak and the opposite loop valleys in the longitudinal direction stand here in a direct contact or even overlap.

In the further course radially away from the connection points, however, the loops run substantially in a circle or curved. But this does not preclude a different course for the loops. According to the invention, $S_1$ has at least the width of a web $S_2$ in the region of the loop line between the loop peak and the loop valley. According to the invention, the web $S_1$ has a shorter length than the web $S_3$, $S_1$ being at most the length, or ¾ the length, preferably at most ⅔ or half the length, especially preferably at most ⅓ the length of $S_3$. A length of $S_1$ is especially preferable which is at most ¼ the length of $S_3$. Preferably, the ratio of $S_2$:$S_1$ is at most 1:2.5, especially at most 1:2.3 or 1:2.1, while at most 1:2.1 and especially at most 1:2 is especially preferred, but at least 1:1.8, preferably at least 1:1.5, especially preferably a ratio of at least 1:1.

The stent according to the invention has acute angles φ in the region of the connection points between loop valleys and loop peaks, which take on a smaller angular dimension under increasing continual expansion or extension of the stent. That is, upon stretching of the stent outwardly in the radial direction, the angle φ becomes smaller and smaller and may take on a condition >=0 at maximum stretching.

Thanks to the arrangement according to the invention, upon stretching of the stent the angles which have their starting points on the loop line in the region between the loop peak and the loop valley decrease continually. Thus, the stent can either be given more flexibility according to the needs of the doctor or of the application and a greater radial force, as would be the case with a large extension, or less flexibility with less radial force, such as would be the case for a small extension. But the design or the structure of the stent does not need to be altered for this.

Furthermore, it is advantageous in these embodiments of the stent according to the invention that during extension or expansion, i.e., an increasing of the diameter of the cavity in the radial direction, the stent does not tear at the connection points, such as may occur in stents of the prior art, since the radial tensile force there occurs principally in the region of the connectors and is not, as with the stent according to the invention, intercepted by the substantially round or curved structure, but with acute angles in the region of the connection points In this way, the mechanical strain in this region is even further reduced with the stent in place, which leads to increased stability.

This structure of the stent according to the invention can also prevent a buckling in the region of the connection points, since here unlike the prior art there are no so-called connectors present, which owing to their length in the longitudinal direction may buckle upon bending of the stent.

Basically the more loops are formed radially within an element, the shorter is the length decrease (shortening) during a longitudinal pull, but the greater is the radial force. However, the stent becomes inflexible. The contrary is the case when fewer loops are laid radially. Here, the radial force of the stent is less, but it becomes on the whole more flexible. Ultimately, however, this kind of conformation of the stent according to the invention produces no danger of injury at least under a uniform pulling in the radial or longitudinal direction, since the stent according to the invention minimizes the action of a pulling force on the connection points both in the radial and in the longitudinal direction. According to the invention, the elements are formed from at least 3 loops each with 3 loop peaks and valleys, while at least 4, especially 5, is preferred. The maximum number of loops is advantageously 10 or 8 loops, while a maximum of 7 loops and especially a maximum of 6 loops is preferred.

The stent according to the invention is preferably designed so that the elements have a maximum in the region of the loop peaks and a minimum in the region of the peak valleys, where the loops of the same element have a length λ in the substantially radial direction y from maximum to maximum and where the loop minimum lies at λ/2 or an odd multiple thereof.

Advantageously, the stent according to the invention has an extension b or b' in the region of the loop peaks and valleys of an element. The loops in the region between neighboring loop peaks and valleys of an element have an extension of a or a', where a or a' is at most equal to the extension b or b', but preferably a or a' is larger than 0 and smaller than b or b' and especially preferably a or a' is equal to 0, but the neighboring loop peaks or valleys of an element are not firmly connected here, i.e., upon expansion of the stent a or a' can become larger than 0. The extensions b, b', a and a' preferably run in the case of an annular or helical shape of the elements substantially parallel with the radial direction, but along the annular or helical shape.

In another embodiment of the stent according to the invention, the extension b or b' has a center point m or m'. The center point m or m' of the extension b or b' lies preferably on the normals N or N', which run orthogonally to the tangent of the loop maximum or minimum.

According to the invention, however, a different conformation of the loop of the stent according to the invention is possible. For example, the loops may be meandering, Ω-shaped or U-shaped. According to the invention, the loops may also have a positive or negative inclination to the radial direction y. Likewise, the loops may have a loop line which is partly or entirely jagged, wavy, formed from individual straight segments, or smooth, and/or otherwise.

The stent according to the invention can be self-expanding or non-self-expanding in design. The expansion of a non-self-expanding stent according to the invention is usually done by means of a balloon catheter, which has previously been introduced into the interior of the stent. Advantageously, however, the stent according to the invention is self-expanding or self-expandable. Prior to the implantation, the stent according to the invention has a slight radial extension and it expands during or after the implantation to a larger radial extension.

In another advantageous embodiment, the stent is formed from a shape memory material or alloy (SMA). Shape memory material has already been used for medical implants in various applications, thus, for example, for stents to stabilize arteries. It is possible in this case to introduce the stent in compressed form into a blood vessel, where it then deploys or expands into an effective form upon contact with the blood at body temperature. In particular, in one advisable embodiment of the stent according to the invention, Nitinol is used, which is a nickel-titanium alloy. However, other alloys are conceivable, such as NiTiCu (nickel-titanium-copper), CuZn (copper-zinc), CuZnAl (copper-zinc-aluminum), CuAlNi (copper-aluminum-nickel), FeNiAl (iron-nickel-aluminum), FeMnSi (iron-manganese-silicon) and/or ZnAuCu (zinc-gold-copper). Likewise, the stent according to the invention can also be made from other materials such as metal, plastic, and/or a combination of the materials mentioned in this paragraph.

In another advantageous embodiment of the stent according to the invention, the stent is radiologically opaque or at least has a radiologically opaque marking. This marking may lie outside and/or inside the stent according to the invention. Thanks to the marking, a better visualization of the stent can be assured during or after the implantation.

Moreover, in an additional embodiment of the stent according to the invention, the stent comprises coupling elements at the longitudinal, axial ends, by which several stents are joined together reversibly directly or indirectly by spacers. This has the advantage that several stents can be placed at the same implantation site or at different implantation sites within an implantation, so that the surgery time can be reduced, for example.

Moreover, although this is not necessary if the stent is cut from a single piece, the stent according to the invention can be electroplated, electropolished and/or mechanically polished at least on one of the surfaces and/or at least at one of the longitudinal, axial ends.

Usually stenoses are dilated by means of a balloon catheter, so that a stent can then be installed. Such dilatations result in vessel damage, which is undesirable to many users (doctors). But thanks to the stent according to the invention, it is possible to install it without previously dilating the stenosis by means of a balloon. Thanks to the outwardly acting (mural) radial force due to the stent according to the invention, it is now possible to place the stent according to the invention in a stenosis and then over the course of several days to outwardly broaden or eliminate the stenosis solely thanks to the stent according to the invention. This, in turn, has the consequence that the surgery time is reduced and vessel damage caused by dilatation by means of balloon catheter can be prevented.

The stent according to the invention is suitable not only for arterial applications, but also for venous applications. With venous stents, they often need to have different diameters on account of the architecture of these vessels. In the prior art, this was solved for example by fashioning the individual elements with different size, so that at the transition from a smaller diameter to a larger diameter regions protrude into the blood stream at the connection points of the individual elements, which in turn may lead to the formation of nonlinear flow and the related deposits.

In another advantageous embodiment of the stent according to the invention, each time two neighboring elements form an element pair and have a length L in the longitudinal direction x). The length L here corresponds at most to 100%, but least to 21%, preferably 75% and especially preferably 50% of the internal diameter of the element pair in the non-expanded condition of the stent.

In another advantageous embodiment of the stent according to the invention, the length L of an element pair each time successively decreases or successively increases in relation to the neighboring element pairs in the longitudinal direction x. In the case of a helical element, the element can also have successively increased or decreased loops within this element. If large loops are formed, then large radii will be produced during dilatation. Thus, slow continuous transitions from large to smaller diameters and vice versa are possible. But these transitions have no points protruding into the blood stream. In particular, large radial forces are needed for small vessel diameters, and these can be realized very well in particular with small loops according to the stent structure according to the invention.

By means of the stent according to the invention, thin and uniformly configured connection points are provided, which hardly change at all the internal volume of the vessel. Even so, the stent according to the invention possesses a large, outwardly directed radial force, which makes it possible to increase the vessel diameter by outward pressure along the entire length of the stent according to the invention and/or to hold it stable.

BRIEF DESCRIPTION OF THE DRAWINGS

The invention shall be described more closely below with the aid of sample embodiments in drawings. The explanations are meant solely as examples and do not limit the general notion of the invention.

There are shown:

FIG. 1 a schematic representation of a stent according to the prior art with a rigid design, so-called Closed Cell Design;

FIG. 2 in a schematic representation of a stent according to the prior art with a partly flexible design, so-called Open Cell Design;

FIGS. 5a to 5c each time in a schematic representation a feature of an embodiment of the stent according to the invention in different states of extension b, b', a and a';

FIG. 7 each time in a schematic representations a feature as well as a detail of the angle φ of an embodiment of the stent according to the invention in different states B, C, D, and E of the extension of the stent.

DETAILED DESCRIPTION OF THE INVENTION

FIG. 1 shows a stent according to the prior art in the so-called rigid or Closed Cell Design. Several elements 300, 310 are arranged in succession in the longitudinal direction x. An element 300 is connected continuously for the entire length in the radial direction y by means of connectors 220 to the following element 310.

FIG. 2 likewise shows a stent according to the prior art, having in part a flexible, so-called Open Cell Design. In this design, an element 300 is connected in the radial direction y by connectors 220 to a neighboring element 310 in the longitudinal direction x. However, there is no continuous connection here in the radial direction y, but instead there are regions in which no connection is present between the elements 300 and 310.

Figure 3:
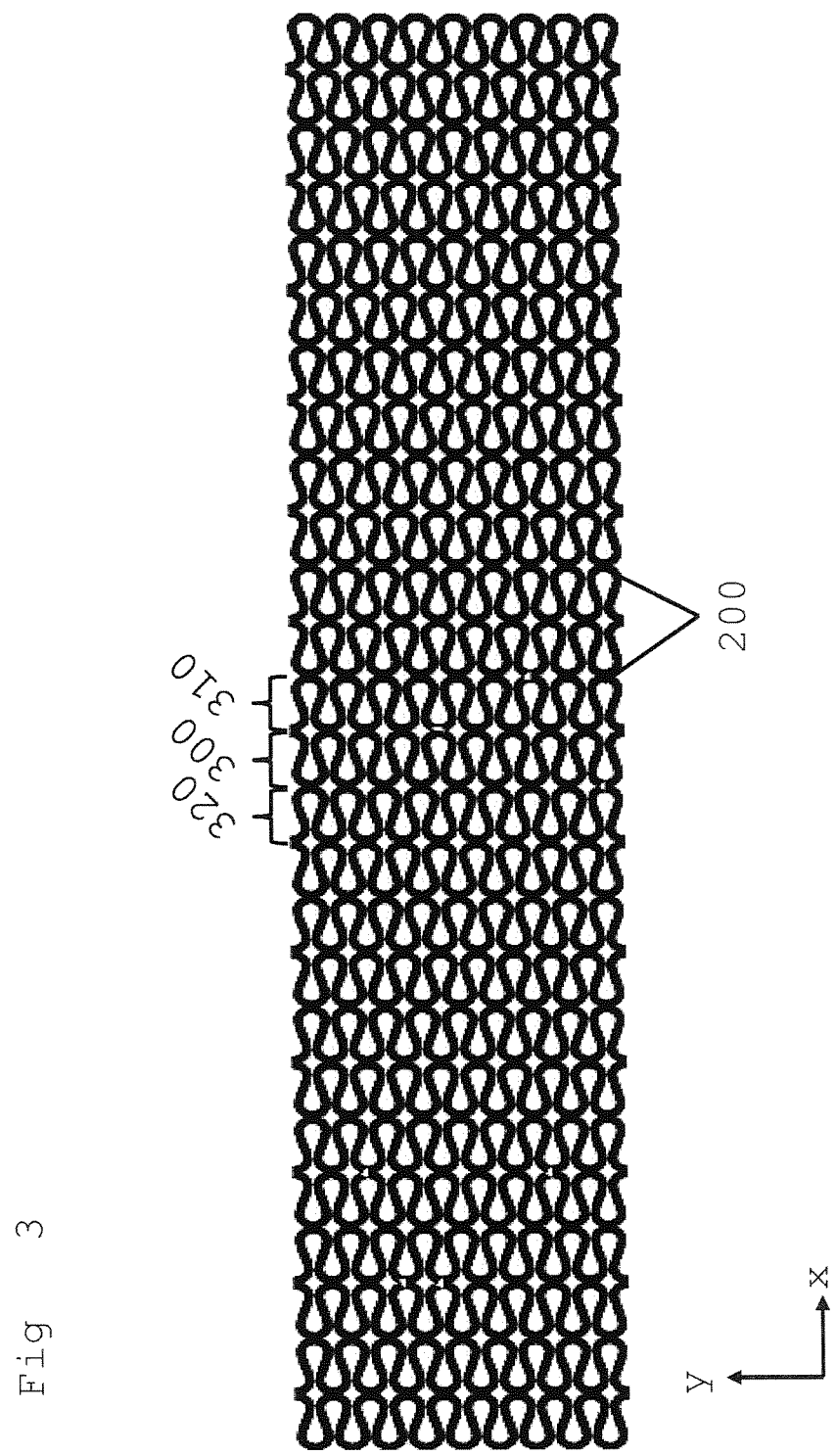
FIG. 3 in a schematic representation an embodiment of the stent according to the invention.

FIG. 3 shows an embodiment of the stent according to the invention, where an element 300 is firmly connected to preceding elements 320 and following elements 310 in the longitudinal direction x by connection points 200. The elements 300, 310, 320 have the shape of loops in the radial direction y with loop peaks and loop valleys.

Figure 4:
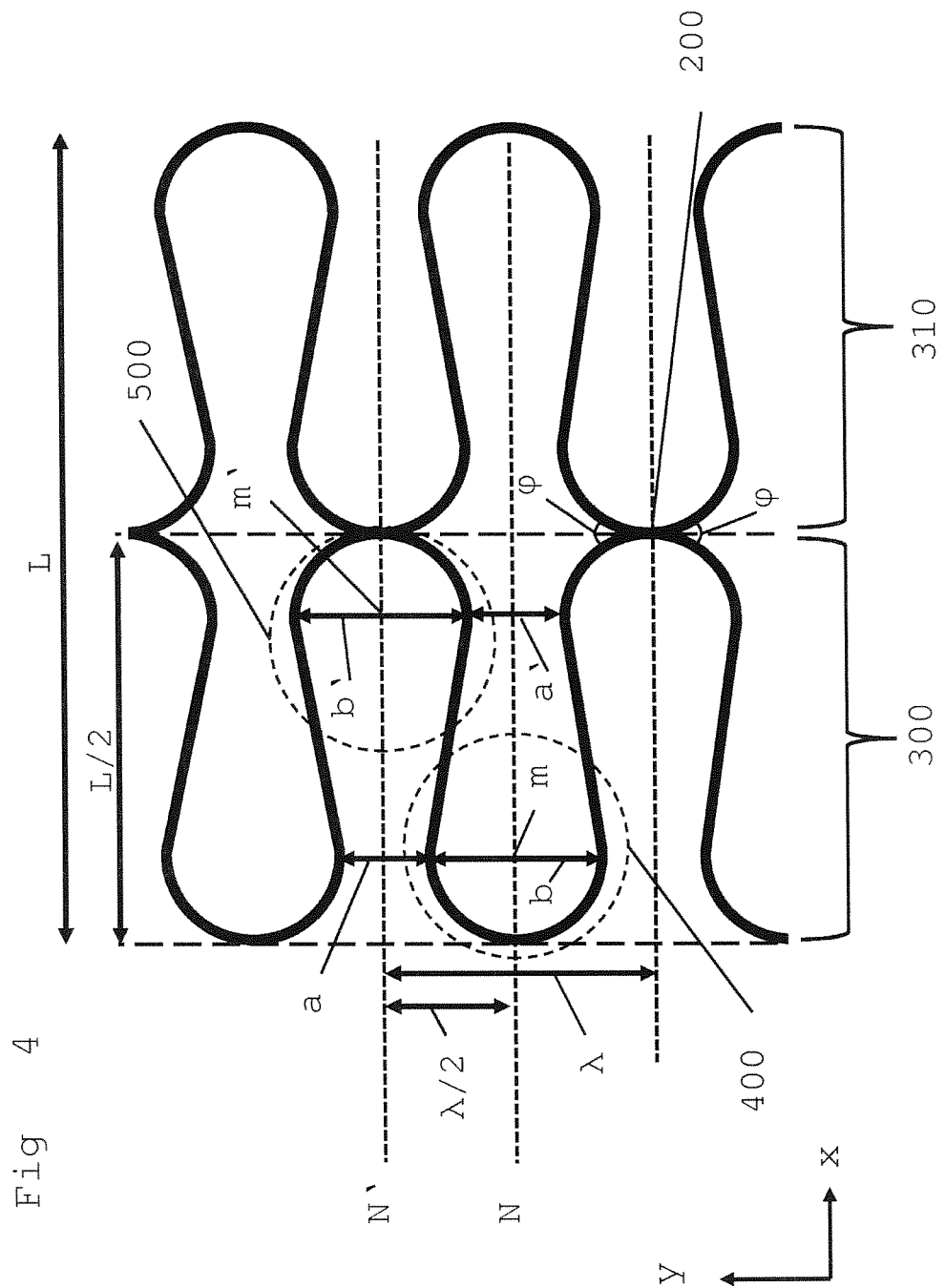
FIG. 4 in a schematic representation a feature of an embodiment of the stent according to the invention.

FIG. 4 shows a schematic detail feature of one embodiment of the stent according to the invention, where an element 300 and its neighboring element 310 following in the longitudinal direction x are represented. The element 300 here has loops with loop peaks 400 and loop valleys 500. The element 300 has a loop length λ from one loop peak to a neighboring loop peak in the radial direction y, while each time the loop valley lies at λ/2. Moreover, the element 300 has a length L/2 from the loop peaks to the loop valleys in the longitudinal direction x. The element pair 300, 310 has a length L in the longitudinal direction x. The element 300 is shifted relative to the following element 310 by a half loop length λ/2, so that its loop valleys are firmly connected to the loop peaks of the following element 310 by connection points 200. Moreover, in the region of the loop peaks and valleys of the element 300 there is represented an extension b or b' with a center point m or m', respectively. The center point m or m' of the extension b or b' in this embodiment lies on the normals N or N' running orthogonally to the tangent of the maximum or minimum of the loop peak or valley.

FIG. 5a shows an embodiment of the stent according to the invention in a state in which the extension a or a' is greater than 0, but smaller than b or b'. By state is meant here a non-expanded state, in which the stent extends even further, i.e., its diameter can further increase outwardly in the radial direction. Moreover, there are shown a web $S_1$, which runs parallel to the longitudinal direction x, and a web $S_3$, which runs parallel to the radial direction y. Moreover, a web $S_2$ is shown, which corresponds to the width of the loop line in the region between the loop peak and the loop valley. It is the case here that $S_1$ has at least the width of $S_2$, and that the web $S_1$ has a shorter length than the web $S_3$. Moreover, the stent has acute angles φ in the region of the connection points between loop valleys and loop peaks, which take on a smaller angular dimension upon expansion of the stent. However, the stent has no so-called connectors, so that no spacings (connectors) are present at the connection points between loop valleys and loop peaks. Instead, the loop valleys and the loop peaks overlap at the connection points according to the invention.

FIG. 5b shows an embodiment of the stent according to the invention in a state in which the extension a or a' is equal to that of b or b'. By state is meant here a non-expanded state, in which the stent extends even further, i.e., its diameter can further increase outwardly in the radial direction.

FIG. 5c shows an embodiment of the stent according to the invention in a state in which the extension a or a' is equal to 0 and b or b' is greater than 0. But the neighboring loop peaks and valleys here are not firmly interconnected in the region of a or a' of an element, i.e., upon an expansion of the stent a or a' can again become larger than 0. By state is meant here a non-expanded state, in which the stent extends even further, i.e., its diameter can further increase outwardly in the radial direction.

Figure 6:
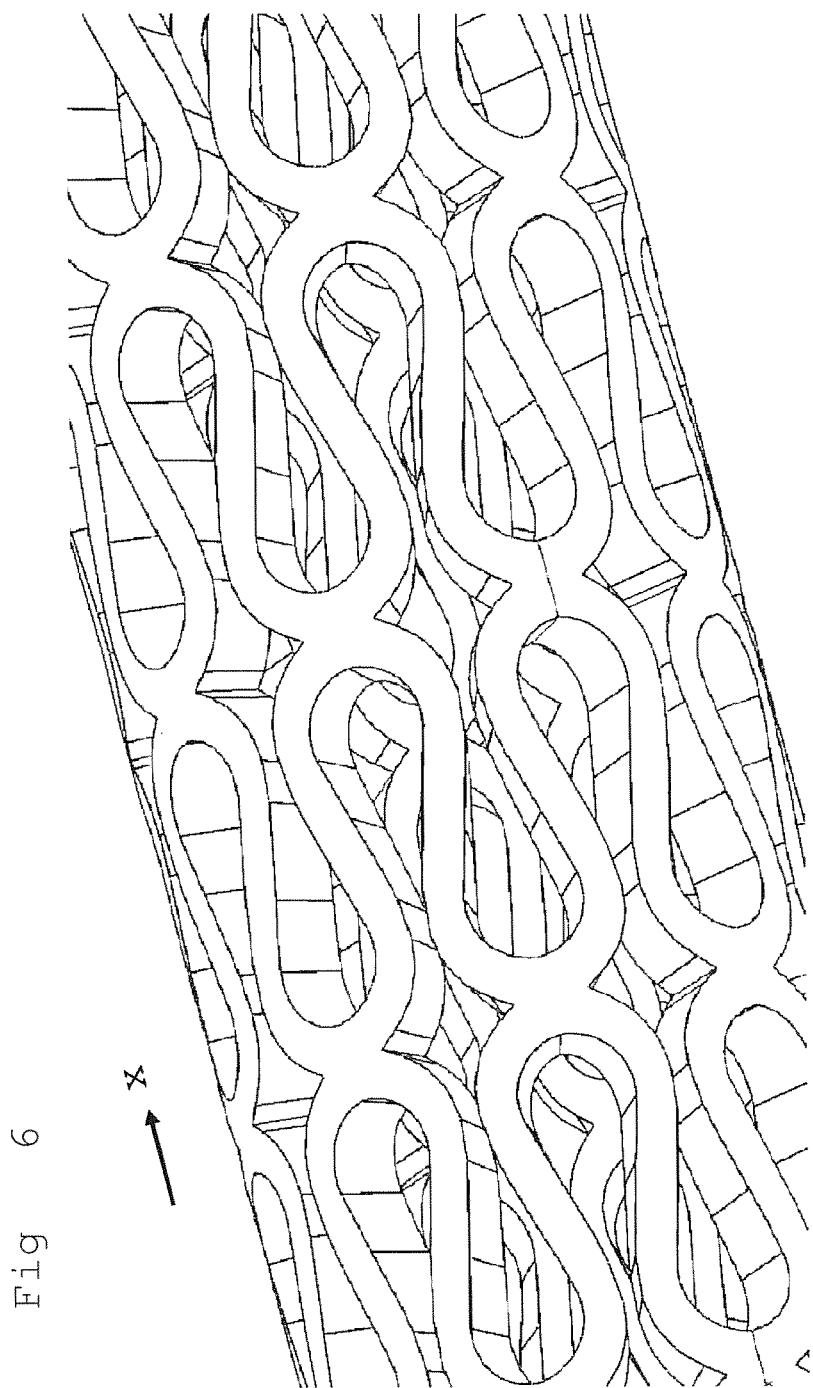
FIG. 6 in a schematic 3D representation a feature of an embodiment of the stent according to the invention.

FIG. 6 shows a detail feature of an embodiment of the stent according to the invention in a schematic 3D representation.

FIG. 7 shows an embodiment of the stent according to the invention in different extension states. The states here range from B, little extended if at all, to C and D, and then to E, very broadly extended, the extension states standing in a relation of E>D>C>B. The acute angle φ, here represented as B1 to E1 depending on the extension state, decreases upon extension from B to E in the relation B1>C1>D1>E1. E1 at maximum extension can take on a value of E1>=0. The angle which has its starting points on the loop line in the region between the loop peak and the loop valley and which is denoted as B0 to E0 also diminishes upon extension from B to E in the relation B0>C0>D0>E0. Thus, the stent can either be given more flexibility and a larger radial force, as would be the case in state E, or less flexibility with lesser radial force, as would be the case for example in state C. However, the design or the structure of the stent does not need to be changed for this.

LIST OF REFERENCES

200 Connection point
210 Non-connected point
220 Connector
300 Element
310 Following element
320 Preceding element
400 Region of the loop peak
500 Region of the loop valley
λ Loop length
λ/2 Half loop length
φ Acute angle
B1 Acute angle φ in extension state B
C1 Acute angle φ in extension state C
D1 Acute angle φ in extension state D
E1 Acute angle φ in extension state E
B0 Angle in extension state B
C0 Angle in extension state C
D0 Angle in extension state D
E0 Angle in extension state E
B Extension state of the stent
C Extension state of the stent
D Extension state of the stent
E Extension state of the stent
a Extension in the region between neighboring loop peaks of an element
a' Extension in the region between neighboring loop valleys of an element
b Extension in the region of a loop peak
b' Extension in the region of a loop valley
L Length of an element pair in longitudinal direction
L/2 Length of an element in longitudinal direction
m Center point of extension b
m' Center point of extension b'
N Normal orthogonal to the tangent of a loop minimum
N' Normal orthogonal to the tangent of a loop minimum
$S_1$ Web in the region of the connection point running substantially parallel to the longitudinal direction
$S_2$ Web in the region of the loop line between the loop peak and the loop valley S₃ Web in the region of the connection point running substantially parallel to the radial direction
x Longitudinal direction
y Radial direction

The invention claimed is:

1. A stent with a continuous, interior, tubular or cylindrical cavity bounded by a wall, wherein the wall is configured to be tubular or cylindrical and extending about an axis running in a longitudinal direction (x) and comprises a structure running about the wall, wherein the structure is formed from elements and the elements are formed from loops, which are arranged substantially in a radial direction (y) about the longitudinal axis, and they have loop peaks and loop valleys arranged in an alternating manner and running substantially parallel to the longitudinal direction (x), so that each of the elements is firmly connected to a preceding or a following element of the elements respectively by connection points in a region of each of the loop valleys of the elements and each of the loop peaks of the following elements and in a region of each of the loop peaks of the elements and each of the loop valleys of the preceding elements in order to produce a one-piece tubular or cylindrical wall structure, wherein all the loop peaks and all the loop valleys opposite to the loop peaks in the longitudinal direction stand in direct contact or overlap each other and for each of the connection points at the connection points a web, $S_1$, running substantially parallel to the longitudinal direction (x) and a web, $S_3$, running substantially parallel to the radial direction (y) is formed, while $S_1$ has at least a width of a web, $S_2$, in a region of a loop line between the loop peaks and the loop valleys and acute angles ($\varphi$) are present in a region of the connection points between the loop valleys and the loop peaks, wherein in an inner region of the loop peaks or valleys of an element of the elements the loop peaks or valleys have an extension b or b', respectively, and the loops in a region between neighboring loop peaks or valleys of an element of the elements have an extension a or a', respectively, wherein within a loop peak of the loop peaks or a loop valley of the loop valleys a or a' is larger than 0 or equal to 0 and smaller than b or b'.

2. The stent according to claim 1, wherein the acute angles ($\varphi$) have their starting points on the loop line in the region between the loop peaks and the loop valleys and the angles ($\varphi$) take on a smaller angular dimension under increasing continual expansion of the stent.

3. The stent according to claim 1, wherein the stent is made from a single tubular piece of material.

4. The stent according to claim 1, wherein the stent is formed from a metal, an alloy, a plastic, a shape memory material, Nitinol, or a combination of these materials.

5. The stent according to claim 1, wherein the loops are formed meandering, Ω-shaped or U-shaped.

6. The stent according to claim 1, wherein the loops have the loop line which is partly or entirely jagged, wavy, formed from individual straight segments, or smooth.

7. The stent according to claim 1, wherein the web $S_1$ has a shorter length than the web $S_3$, $S_1$ being at most ¾ or at most ⅔ or at most ½ or at most ⅓ or at most ¼ a length of $S_3$.

8. The stent according to claim 1, wherein the stent is radiologically opaque or at least has a radiologically opaque marking.

9. The stent according to claim 1, wherein the stent comprises coupling elements at longitudinal, axial ends, by which several stents are reversibly joined together directly or indirectly by spacers.

10. The stent according to claim 1, wherein the stent is electroplated, electropolished and/or mechanically polished at least on one surface and/or at least at one of longitudinal, axial ends.

11. The stent according to claim 1, wherein the elements have a maximum in the region of the loop peaks and a minimum in the region of the peak valleys, where the loops have a length λ in the radial direction (y) from maximum to maximum of the same element and where the loop minimum lies at λ/2 or an odd multiple thereof.

12. The stent according to claim 1, wherein the elements are formed from at least 3 loops each with 3 loop peaks and valleys.

13. The stent according to claim 1, wherein in the inner region of the loop peaks or valleys of an element of the elements the loop peaks or valleys have the extension b or b', respectively, and the loops in the region between the neighboring loop peaks or valleys of an element of the elements have the extension a or a', respectively, where the neighboring loop peaks or valleys of an element of the elements are not firmly connected here.

14. The stent according to claim 13, wherein a length L of an element pair successively decreases in relation to neighboring element pairs in the longitudinal direction (x) so as to allow slow continuous transitions from large to smaller diameters of the element pairs.

15. The stent according to claim 1, wherein for each of the connection points two neighboring elements form an element pair and have a length L in the longitudinal direction (x), where the length L corresponds at most to 100% or 75% or 50% or at least to 21% of an internal diameter of the element pair in a non-expanded condition of the stent.

16. The stent according to claim 1, wherein the elements are all identical.

17. A stent with a continuous, interior, tubular or cylindrical cavity bounded by a wall, wherein the wall is configured to be tubular or cylindrical and extending about an axis running in a longitudinal direction (x) and comprises a structure running about the wall, wherein the structure is formed from elements and the elements are formed from loops, which are arranged substantially in a radial direction (y) about the longitudinal axis, and they have loop peaks and loop valleys arranged in an alternating manner and running substantially parallel to the longitudinal direction (x), so that an element of the elements is firmly connected to a preceding or a following element of the elements by connection points in a region of the loop valleys of the elements and the loop peaks of following elements and in a region of the loop peaks of the elements and the loop valleys of preceding elements in order to produce a one-piece tubular or cylindrical wall structure, wherein the loop peaks and the loop valleys opposite to the loop peaks in the longitudinal direction stand in direct contact or overlap each other and for each of the connection points at the connection points a web, $S_1$, running substantially parallel to the longitudinal direction (x) and a web, $S_3$, running substantially parallel to the radial direction (y) is formed, while $S_1$ has at least a width of a web, $S_2$, in a region of a loop line between the loop peaks and the loop valleys and acute angles ($\varphi$) are present in a region of the connection points between the loop valleys and the loop peaks, wherein in an inner region of the loop peaks or valleys of an element of the elements the loop peaks or valleys have an extension b or b', respectively, and the loops in a region between neighboring loop peaks or valleys of an element of the elements have an extension a or a', respectively, wherein within a loop peak of the loop peaks or a loop valley of the loop valleys a or a' is larger than 0 or equal to 0 and smaller than b or b', wherein a length L of an element pair successively decreases in relation to neighboring element pairs in the longitudinal direction (x) so as to allow slow continuous transitions from large to smaller diameters of the element pairs.

18. The stent according to claim 17, wherein each of the elements is firmly connected to a preceding or a following element of the elements respectively by connection points in a region of each of the loop valleys of the elements and each of the loop peaks of the following elements and in a region of each of the loop peaks of the elements and each of the loop valleys of the preceding elements, wherein all the loop peaks and all the loop valleys opposite to the loop peaks in the longitudinal direction stand in direct contact or overlap each other.

* * * * *